United States Patent [19]

Belley

[11] Patent Number: 5,212,180
[45] Date of Patent: May 18, 1993

[54] QUINOLINE-CONTAINING KETOACIDS AS LEUKOTRIENE ANTAGONISTS

[75] Inventor: Michel L. Belley, Pierrefonds, Canada

[73] Assignee: Merck Frosst Canada, Inc., Kirkland, Canada

[21] Appl. No.: 832,298

[22] Filed: Feb. 7, 1992

Related U.S. Application Data

[63] Continuation-in-part of Ser. No. 658,931, Feb. 21, 1991, abandoned.

[51] Int. Cl.$^5$ .................. H01N 43/42; C07D 215/36
[52] U.S. Cl. ..................................... 514/311; 546/172
[58] Field of Search .................. 546/172, 173; 514/311

[56] References Cited

FOREIGN PATENT DOCUMENTS 0233763  8/1987  European Pat. Off. .

Primary Examiner—C. Warren Ivy
Assistant Examiner—Raymond Covington
Attorney, Agent, or Firm—Gabriel Lopez; Joseph F. DiPrima

[57] ABSTRACT

Compounds having the formula I:

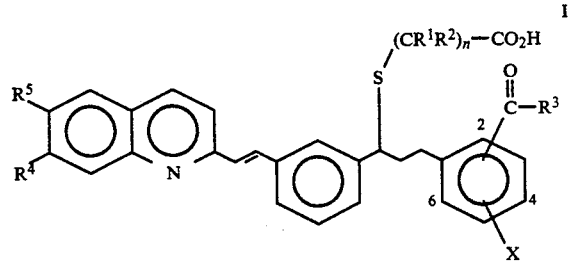

are antagonists of the actions of leukotrienes. These compounds are useful as anti-asthmatic, anti-allergic, anti-inflammatory, and cytoprotective agents. They are also useful in treating angina, cerebral spasm, glomerular nephritis, hepatitis, endotoxemia, uveitis and allograft rejection.

9 Claims, No Drawings

QUINOLINE-CONTAINING KETOACIDS AS LEUKOTRIENE ANTAGONISTS

CROSS-REFERENCE

This is a continuation-in-part of U.S. Ser. No. 658,931, Feb. 21, 1991, now abandoned.

BACKGROUND OF THE INVENTION

The leukotrienes constitute a group of locally acting hormones, produced in living systems from arachidonic acid. The major leukotrienes are Leukotriene B4 (abbreviated at LTB4), LTC4, LTD4 and LTE4. The biosynthesis of these leukotrienes begins with the action of the enzyme 5-lipoxygenase on arachidonic acid to produce the epoxide known as Leukotriene A4 (LTA4), which is converted to the other leukotrienes by subsequent enzymatic steps. Further details of the biosynthesis as well as the metabolism of the leukotrienes are to be found in the book Leukotrienes and Lipoxygenases, ed. J. Rokach, Elsevier, Amsterdam (1989). The actions of the leukotrienes in living systems and their contribution to various diseases states are also discussed in the book by Rokach.

European patent applications 318,093 (May 31, 1989) and 399,818 (Nov. 28, 1990) disclose generic structures somewhat similar to the present compounds although there are no aliphatic ketones present in them. European patent applications 349,062 (Jan. 3, 1990) and 399,291 (Nov. 28, 1990, Bayer) describe quinoline-containing leukotriene biosynthesis inhibitors, which differ from the present compound most notably in that the quinoline moiety is joined to the remainder of the molecule by an ether link rather than a vinyl group. The structures of the compounds disclosed in the above patent applications are shown below.

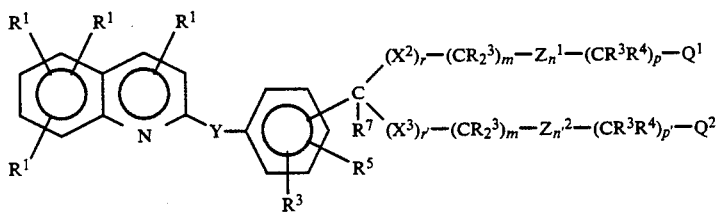

EP 318, 093
Merck

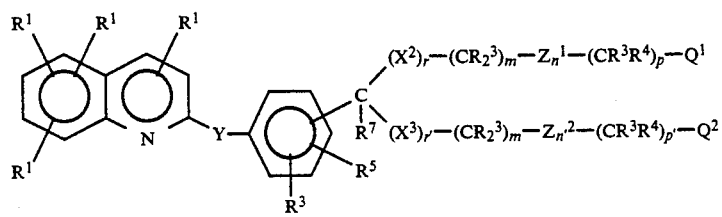

EP 399, 818
Merck

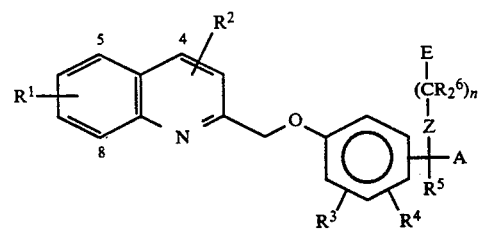

EP 349, 062
Merck

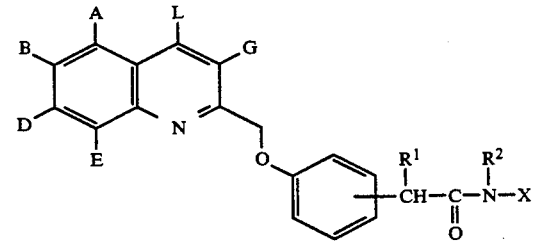

EP 399, 291
Bayer

SUMMARY OF THE INVENTION

The present invention relates to quinoline-containing ketoacids having activity as leukotriene antagonists, to methods for their preparation, and to methods and pharmaceutical formulations for using these compounds in mammals (especially humans).

Because of their activity as leukotriene antagonists, the compounds of the present invention are useful as anti-asthmatic, anti-allergic, anti-inflammatory and cytoprotective agents. They are also useful in treating angina, cerebral spasm, glomerular nephritis, hepatitis, endotoxemia, uveitis and allograft rejection.

DETAILED DESCRIPTION OF THE INVENTION

The compounds of the present invention are represented by Formula I:

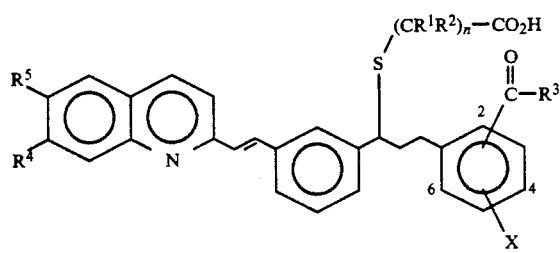

wherein:
each of $R^1$ and $R^2$ is independently H or lower alkyl, or $R^1$ and $R^2$ attached to the same carbon are a ring of 3 to 6 carbon atoms;
$R^3$ is $C_1$–$C_3$ alkyl;
$R^4$ is Cl or Br;
$R^5$ is H, Cl or Br;
X is H or Cl;
n is 1 to 4;
or a pharmaceutically acceptable salt thereof.

A preferred embodiment of the invention is a compound of Formula I represented by Formula Ia:

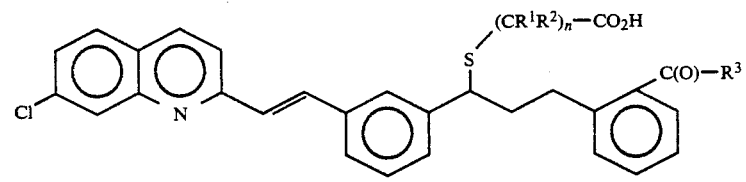

DEFINITIONS

The following abbreviations have the indicated meanings:

| | |
|---|---|
| Ac = | acetyl |
| n-Bu = | normal butyl |
| t-Bu = | tertiary butyl |
| Et = | ethyl |
| Me = | methyl |
| Ph = | phenyl |
| Tz = | 1H (or 2H)-tetrazol-5-yl |
| r.t. = | room temperature |
| rac. = | racemic |
| THF = | tetrahydrofuran |
| Ms = | methanesulfonate = mesylate |
| LDA = | lithium diisopropylamide |
| DMF = | N,N-dimethylformamide |
| $Et_3N$ = | triethylamine |
| DMSO = | dimethylsulfoxide |
| NSAID = | non-steroidal antiinflammatory drug |

"Lower alkyl" means alkyl groups of from 1 to 7 carbon atoms. Examples of lower alkyl groups include methyl, ethyl, propyl, isopropyl, butyl, s-and t-butyl, pentyl, hexyl, heptyl, and the like.

OPTICAL ISOMERS—DIASTEREOMERS—GEOMETRIC ISOMERS

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

The compounds described herein contain olefinic double bonds, and unless specified otherwise, are meant to include both E and Z geometric isomers.

SALTS

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

It will be understood that in the discussion of methods of treatment which follows, references to the compounds of Formula I are meant to also include the pharmaceutically acceptable salts.

UTILITIES

The ability of the compounds of Formula I to antagonize the actions of the leukotrienes makes them useful for preventing or reversing the symptoms induced by the leukotrienes in a human subject. This antagonism of the actions of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as psoriasis, atopic eczema, and the like, 6) cardiovascular disorders such as angina, myocardial ischemia, hypertension, platelet aggregation and the like, 7) renal insufficiency arising from ischaemia induced by immunological or chemical (cyclosporin) etiology, 8) migraine or cluster headache, 9) ocular conditions such as uveitis, 10) hepatitis resulting from chemical, immunological or infectious stimuli, 11) trauma or shock states such as burn injuries, endotoxemia and the like, 12) allograft rejection, 13) prevention of side effects associated with therapeutic administration of cytokines such as Interleukin II and tumor necrosis factor, 14) chronic lung diseases such as cystic fibrosis, bronchitis and other small and large-airway diseases, and 15) cholecystitis.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as CCl4 and D-galactosamine; ischemic renal failure; disease-induced hepatic damage; bile salt induced pancreatic or gastric damage; trauma- or stress-induced cell damage; and glycerol- induced renal failure. The compounds also exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay and are described in

DOSE RANGES

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001-1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with an NSAID that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

PHARMACEUTICAL COMPOSITIONS

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of compound I in suitable propellants, such as fluorocarbons or hydrocarbons.

Suitable topical formulations of Compound I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |
| Tablet | mg/tablet |
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |
| Capsule | mg/capsule |
| Compound of Formula I | 25 |
| Lactose Powder | 573.5 |
| Magnesium Stearate | 1.5 |
| | 600 |
| Aerosol | Per canister |
| Compound of Formula I | 24 mg |
| Lecithin, NF Liquid Concentrate | 1.2 mg |
| Trichlorofluoromethane, NF | 4.025 gm |
| Dichlorodifluoromethane, NF | 12.15 gm |

COMBINATIONS WITH OTHER DRUGS

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac. Structually related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

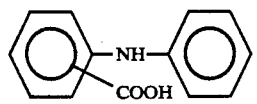

which can bear a variety of substitutents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

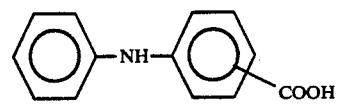

which can bear a variety of substitutents and in which the free —COOH group can be in the form of a pharmaceutically acceptable salt group, e.g., —COO$^-$Na$^+$.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

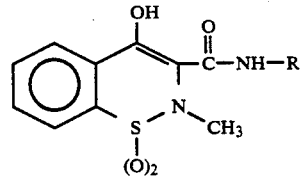

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid and ufenamate.

The following NSAIDs, designated by company code number (see e.g., Pharmaprojects), may also be used: 480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDs are acetyl salicylic acid, diclofenac, fenbufen, fenoprofen, flurbiprofen, ibuprofen, ketoprofen, naproxen, phenylbutazone, piroxicam, sulindac and tolmetin.

Pharmaceutical compositions comprising the Formula I compounds may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982) and 61,800 (Jun. 10, 1982); and in U.K. Patent Specification No. 2,058,785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as a-fluoromethylhistidine, described in U.S. Pat. No. 4,325,961. The compounds of the Formula I may also be advantageously combined with an $H_1$- or $H_2$-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in Nature, Vol. 316, pages 126-131, 1985, and the like. Each of the references referred to in this paragraph is hereby incorporated herein by reference.

Other advantageous pharmaceutical compositions comprise the Formula I compounds in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

METHODS OF SYNTHESIS

Compounds of the present invention can be prepared according to the following methods. Temperatures are in degrees Celsius.

SCHEME 1

Aldehyde II (U.S. Pat. No. 4,851,409, Example 24, Step 1) is reacted with vinyl magnesium bromide in a suitable solvent such as toluene, THF, ether or mixtures thereof. The allylic carbinol III so obtained is coupled with the aromatic halide IV using a palladium acetate catalyst system to yield ketoester V. Reduction of the ketone group of V with the complex VI (J. Am. Chem. Soc. 104, 5551-3 (1987)) and borane in THF gives the diastereoisomer VII.

The ester group in VII may be converted directly to a ketone (IX) by treatment with 2 equivalents of MeOH followed by 8 equivalents of alkyl Grignard reagent. The use of a small amount of MeOH gives improved yields in this reaction. Alternatively, VII may be reacted with N,O-dimethylhydroxylamine to give the N-methyl N-methoxyamide VIII, which upon treatment with an alkyl Grignard reagent yields ketone IX. Ketoalcohol IX is then converted to XI (I) by a standard set of reactions involving formation of the methanesulfonate of the alcohol and its displacement by thiol X under basic conditions.

It will be obvious to one skilled in the art that compound XI having the opposite stereochemistry at the sulfur bearing benzylic carbon can be obtained by using the opposite stereoisomer of the reduction catalyst VI, or by inversion of the stereocenter in VII or IX by a Mitsunobu reaction (Synthesis, 1-28, 1981).

SCHEME 2

An alternative synthesis of XI involves introducing the sulfur containing acid side chain into VII prior to converting the ester group of VII into a ketone. In this way, intermediates XII and XIII are obtained using procedures similar to those described in Scheme 1.

SCHEME 3

Methodology for preparing representative optically active precursors for the sulfur containing acid side chain are indicated in Scheme 3. The commercially available alcohol XIV is converted to the intermediate XV by treatment with diethylazodicarboxylate (DEAD), triphenylphosphine (Ph$_3$P) and thiolacetic acid (HSAc).

Diastereoselective methylation of XIV is carried out by formation of a dianion with LDA and reaction with methyl iodide. The resulting methylated alcohol is converted to XVI, which is transformed to the thiol XVII by standard demethylation and hydrolysis procedures.

It will be obvious to one skilled in the art that by starting with the alcohol of stereochemistry opposite to that of XIV, the opposite isomers of XV and XVII will be obtained.

SCHEME 4

The mesylate XVIII of alcohol IX can be treated with XV and hydrazine in a suitable solvent such as THF, MeOH, t-BuOH or mixtures thereof, to yield the intermediate XIX. The later can be hydrolyzed under standard conditions to yield the product XX (I). It will be obvious to one skilled in the art that the thiol corresponding to XV could also be used in this procedure.

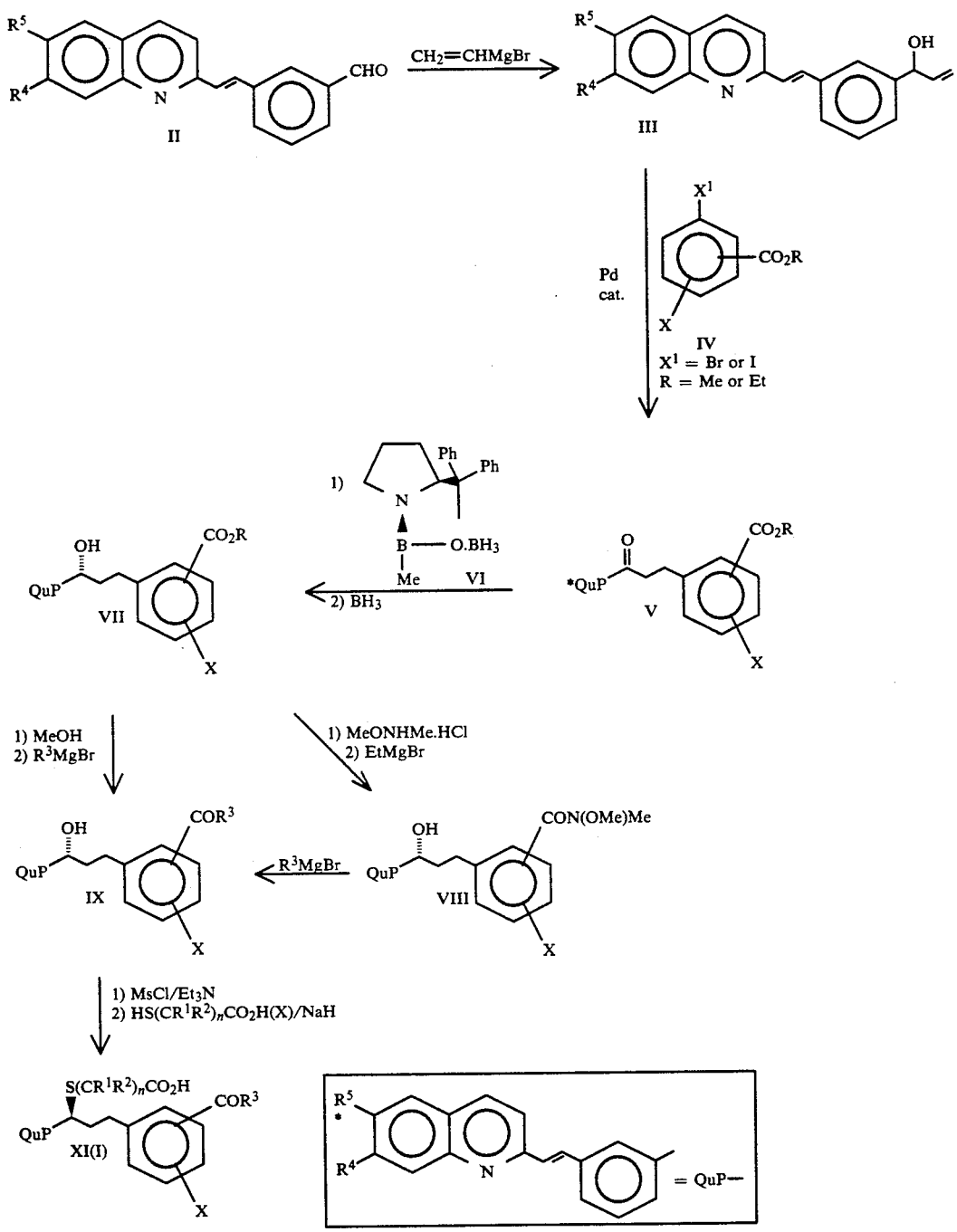
SCHEME 1
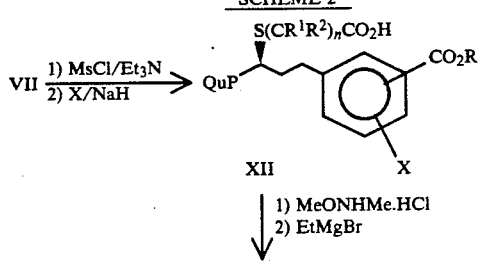
SCHEME 2
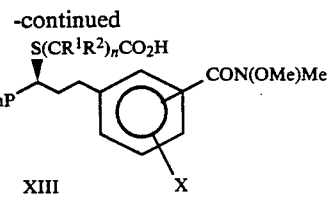
SCHEME 3

-continued

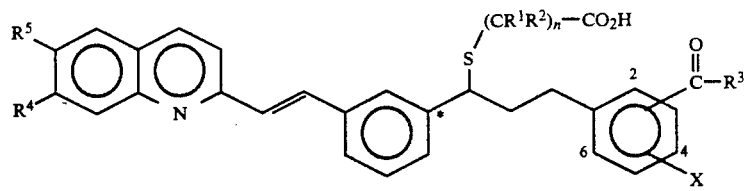

XIV → XV

1) LDA
2) MeI
3) DEAD/Ph₃P/HSAc

REPRESENTATIVE COMPOUNDS

Table I illustrates compounds representative of the present invention.

TABLE I

| Ex. No. | $R^4$ | $R^5$ | $(CR^1R^2)_n$ | Stereo * | $R^3$ | Ketone Position | X |
|---|---|---|---|---|---|---|---|
| 1 | Cl | H | $CH_2(S)CH(CH_3)$ | (S) | $CH_3$ | 2- | H |
| 2 | Cl | H | $CH_2(S)CH(CH_3)$ | (S) | $CH_2CH_3$ | 2- | H |
| 3 | Cl | H | $CH_2(S)CH(CH_3)$ | (S) | $CH_3$ | 3- | H |
| 4 | Cl | H | rac-$CH(CH_3)CH_2$ | (R) | $CH_3$ | 2- | H |
| 5 | Cl | H | $CH_2(S)CH(CH_3)$ | (S) | $CH_3$ | 2- | 4-Cl |
| 6 | Cl | H | $CH_2(S)CH(CH_2CH_3)$ | (S) | $CH_3$ | 2- | H |
| 7 | Cl | H | $(S)CH(CH_3)CH_2$ | (R) | $CH_3$ | 2- | H |
| 8 | Cl | H | $(R)CH(CH_3)CH_2$ | (R) | $CH_3$ | 2- | H |
| 9 | Cl | H | $CH_2C(CH_3)_2CH_2$ | (R) | $CH_3$ | 2- | H |
| 10 | Cl | H | $(S)CH(CH_3)CH_2CH_2$ | (R) | $CH_3$ | 2- | H |
| 11 | Cl | H | $CH_2(S)CH(CH_3)$ | (S) | $CH_3$ | 4- | H |
| 12 | Cl | H | $(S)CH(CH_2CH_3)CH_2$ | (R) | $CH_3$ | 2- | H |
| 13 | Cl | H | $(R)CH(CH_2CH_3)CH_2$ | (R) | $CH_3$ | 2- | H |
| 14 | Br | H | $CH_2(S)CH(CH_3)$ | (S) | $CH_3$ | 2- | H |
| 15 | Cl | H | $(S)CH(CH_3)(S)CH(CH_3)$ | (R) | $CH_3$ | 2- | H |
| 16 | Cl | Cl | $CH_2(S)CH(CH_3)$ | (S) | $CH_3$ | 2- | H |
| 17 | Cl | H | $CH_2C(CH_2CH_2)CH_2$ | (R) | $CH_3$ | 2- | H |

ASSAYS FOR DETERMINING BIOLOGICAL ACTIVITY

The leukotriene antagonist properties of the compounds of the present invention were evaluated using the following assays.

LTD₄ RECEPTOR BINDING STUDIES IN GUINEA PIG LUNG MEMBRANES, GUINEA PIG TRACHEA AND IN VIVO STUDIES IN ANESTHETIZED GUINEA PIGS

A complete description of these three tests is given by T. R. Jones et al., Can. J. Physiol. Pharmacol., 67, 17–28 (1989).

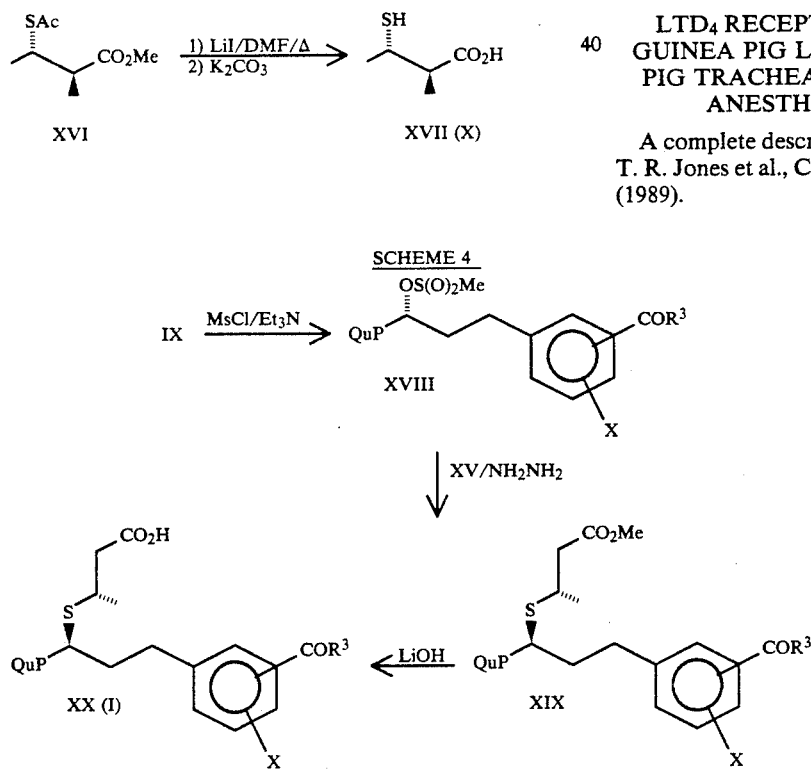

ASTHMATIC RAT ASSAY

Rats are obtained from an inbred line of asthmatic rats. Both female (190-250 g) and male (260-400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate was supplied by Sandoz Ltd., Basel.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a DeVilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 mL of a suspension containing 1 mg EA and 200 mg aluminum hydroxide in saline. They are used between days 12 and 24 postsensitization. In order to eliminate the serotonin component of the response, rats are pretreated intravenously 5 minutes prior to aerosol challenge with 3.0 mg/kg of methysergide. Rats are then exposed to an aerosol of 3% EA in saline for exactly 1 minute, then their respiratory profiles are recorded for a further 30 minutes. The duration of continuous dyspnea is measured from the respiratory recordings.

Compounds are generally administered either orally 1-4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. Their activity is determined in terms of their ability to decrease the duration of symptoms of dyspnea in comparison with a group of vehicle-treated controls. Usually, a compound is evaluated at a series of doses and an $ED_{50}$ is determined. This is defined as the dose (mg/kg) which would inhibit the duration of symptoms by 50%.

PULMONARY MECHANICS IN TRAINED CONSCIOUS SQUIRREL MONKEYS

The test procedure involves placing trained squirrel monkeys in chairs in aerosol exposure chambers. For control purposes, pulmonary mechanics measurements of respiratory parameters are recorded for a period of about 30 minutes to establish each monkey's normal control values for that day. For oral administration, compounds are dissolved or suspended in a 1% methocel solution (methylcellulose, 65HG, 400 cps) and given in a volume of 1 ml/kg body weight. For aerosol administration of compounds, a DeVilbiss ultrasonic nebulizer is utilized. Pretreatment periods vary from 5 minutes to 4 hours before the monkeys are challenged with aerosol doses of either leukotriene $D_4$ ($LTD_4$) or Ascaris antigen.

Following challenge, each minute of data is calculated by computer as a percent change from control values for each respiratory parameter including airway resistance ($R_L$) and dynamic compliance ($C_{dyn}$). The results for each test compound are subsequently obtained for a minimum period of 60 minutes post challenge which are then compared to previously obtained historical baseline control values for that monkey. In addition, the overall values for 60 minutes post-challenge for each monkey (historical baseline values and test values) are averaged separately and are used to calculate the overall percent inhibition of $LTD_4$ or Ascaris antigen response by the test compound. For statistical analysis, paired t-test is used. (References: McFarlane, C. S. et al., Prostaglandins, 28:173-182, 1984, McFarlane, C. S. et al., Agents Actions 22:63-68, 1987.)

PREVENTION OF INDUCED BRONCHOCONSTRICTION IN ALLERGIC SHEEP

A. Rationale:

Certain allergic sheep with known sensitivity to a specific antigen (Ascaris suum) respond to inhalation challenge with acute and late bronchial responses. The time course of both the acute and the late bronchial responses approximates the time course observed in asthmatics and the pharmacological modification of both responses is similar to that found in man. The effects of antigen in these sheep are largely observed in the large airways and are conveniently monitored as changes in lung resistance or specific lung resistance.

B. Methods:

Animal Preparation: Adult sheep with a mean weight of 35 kg (range, 18 to 50 kg) are used. All animals used meet two criteria: a) they have a natural cutaneous reaction to 1:1,000 or 1:10,000 dilutions of *Ascaris suum* extract (Greer Diagnostics, Lenois, NC) and b) they have previously responded to inhalation challenge with *Ascaris suum* with both an acute bronchoconstriction and a late bronchial obstruction (Abraham, W. M., Delehung, J. C., Yerger, L. and Merchette, B., Am. Rev. Resp. Dis., 1983, 128, 839-44).

Measurement of Airway Mechanics: The unsedated sheep are restrained in a cart in the prone position with their heads immobilized. After topical anesthesia of the nasal passages with 2% lidocaine solution, a balloon catheter is advanced through one nostril into the lower esophagus. The animals are then intubated with a cuffed endotracheal tube through the other nostril using a flexible fiberoptic bronchoscope as a guide. Pleural pressure is estimated with the esophageal balloon catheter (filled with one ml of air), which is positioned such that inspiration produces a negative pressure deflection with clearly discernible cardiogenic oscillations. Lateral pressure in the trachea is measured with a sidehole catheter (inner dimension, 2.5 mm) advanced through and positioned distal to the tip of the nasotracheal tube. Transpulmonary pressure, the difference between tracheal pressure and pleural pressure, is measured with a differential pressure transducer (DP45; Validyne Corp., Northridge, Calif.). For the measurement of pulmonary resistance ($R_L$), the maximal end of the nasotracheal tube is connected to a pneumotachograph (Fleisch, Dyna Sciences, Blue Bell, Pa.). The signals of flow and transpulmonary pressure are recorded on an oscilloscope (Model DR-12; Electronics for Medicine, White Plains, N.Y.) which is linked to a PDP-11 Digital computer (Digital Equipment Corp., Maynard, Mass.) for on-line calculation of $R_L$ from transpulmonary pressure, respiratory volume obtained by integration and flow. Analysis of 10-15 breaths is used for the determination of $R_L$. Thoracic gas volume ($V_{tg}$) is measured in a body plethysmograph, to obtain specific pulmonary resistance ($SR_L = R_L \cdot V_{tg}$).

Aerosol Delivery Systems: Aerosols of *Ascaris suum* extract (1:20) are generated using a disposable medical-nebulizer (Raindrop®, Puritan Bennett), which produces an aerosol with a mass median aerodynamic diameter of 6.2 μM (geometric standard deviation, 2.1) as determined by an electric size analyzer (Model 3030; Thermal Systems, St. Paul, Minn.). The output from the nebulizer is directed into a plastic t-piece, one end of which is attached to the nasotracheal tube, the other end of which is connected to the inspiratory part of a Harvard respirator. The aerosol is delivered at a tidal volume of 500 ml of a rate of 20 per minute. Thus, each sheep receives an equivalent dose of antigen in both placebo and drug trials.

Experimental Protocol: Prior to antigen challenge baseline measurements of $SR_L$ are obtained, infusion of the test compound is started 1 hour prior to challenge, the measurement of $SR_L$ repeated and then the sheep undergoes inhalation challenge with *Ascaris suum* antigen. Measurements of $SR_L$ are obtained immediately after antigen challenge and a 1, 2, 3, 4, 5, 6, 6.5, 7, 7.5 and 8 hours after antigen challenge. Placebo and drug tests are separated by at least 14 days. In a further study, sheep are given a bolus dose of the test compound followed by an infusion of the test compound for 0.5–1 hour prior to ascaris challenge and for 8 hours after ascaris as described above.

Statistical Analysis: A Kruskal-Wallis one way ANOVA test is used to compare the acute immediate responses to antigen and the peak late response in the controls and the drug treated animals.

The invention is further defined by reference to the following examples, which are intended to be illustrative and not limiting. All temperatures are in degrees Celsius.

EXAMPLE 1

Sodium 3-((1(S)-(3-(2-(7-chloro-2-quinolinyl)ethenyl)phenyl)-3-(2-acetylphenyl)propyl)thio)-2(S)-methylpropanoate Step 1: 1-(3-(2-(7-Chloro-2-quinolinyl)ethenyl)-phenyl)-2-propen-1-ol To a degassed suspension of 3-(2-(7-chloro-2-quinolinyl)ethenyl)benzaldehyde (U.S. Pat. No. 4,851,409, Example 24, Step 1) (100 g, 0.34 mol) in toluene (700 mL) at 0° C. was slowly added 1.0M vinylmagnesium bromide in toluene/THF (370 mL, 0.37 mol). After stirring for 1 hour at 0° C., the reaction was quenched by the slow addition of saturated $NH_4Cl$ solution (150 ml), followed by $H_2O$ (500 mL) and HOAc (50 mL). The product was extracted with EtOAc and the two-phase system was filtered through celite to remove an insoluble precipitate. The aqueous phase was then re-extracted with EtOAc (100 mL) and the combined organic layer was washed with $H_2O$, followed by brine. The solution was dried ($MgSO_4$), and evaporated to give a dark yellow residue which was purified by flash chromatography (EtOAc:hexane 1:5, then 1:3). The product was filtered from the column fractions to give a beige solid (67.6 g, mp=110°–112° C.). The filtrate was concentrated and the resulting residue was recrystallized from EtOAc/hexane 1:4 to give a second crop of 15.1 g.

Step 2: Methyl 2-(3-(3-(2-(7-chloro-2-quinolinyl)ethenyl)phenyl)-3-oxopropyl)benzoate A degassed suspension of the product of Step 1 (50.3 g, 156 mmol), n-$Bu_4NCl$ (86.0 g, 312 mmol), LiOAc.2-$H_2O$ (41.2 g, 390 mmol), LiCl (6.84 g, 156 mmol), $Pd(OAc)_2$ (1.00 g, 4.7 mmol), and methyl 2-iodobenzoate (41.00 g, 156 mmol) in DMF (300 mL) was stirred for 3 hours at 90° C. The dark red solution was then cooled to r.t. and poured into 2 L of ice cold $H_2O$. The product was extracted with hot EtOAc, dried over $Na_2SO_4$, filtered and concentrated to dryness. It was dissolved in 600 ml of hot toluene and filtered through a small silica pad (1 L). The title product was finally recrystallized from EtOAc:hexane 1:1 (1.2 L). The title product was finally recrystallized from EtOAc:hexane 1:1 (1.2 L). Recrystallization of the mother liquors in EtOAc:hexane 1:3 (400 mL) afforded a second crop of the title compound.

$^1H$ NMR ($CDCl_3$): δ3.40 (4H, s), 3.92 (3H, s), 7.25–7.52 (6H, m), 7.63 (1H, d), 7.70–7.82 (3H, m), 7.95 (2H, d) 8.05 (1H, br s), 8.11 (1H, d), 8.29 (1H, br s).

Step 3: Methyl 2-(3-(3-(2-(7-chloro-2-quinolinyl)ethenyl)phenyl)-3(R)-hydroxypropyl)benzoate At −20° C., a solution of (S)-tetrahydro-1-methyl-3,3-diphenyl-1H,3H-pyrrolo(1,2-c) (1,3,2,) oxazaborole.borane complex (J. Am. Chem. Soc., 104, 5551–5553 (1987) 6.34 g, 21.8 mmol) in anhydrous THF (20 ml) was added dropwise to a solution of the ketone of Step 2 (33.1 g, 72.6 mmol) in THF (300 mL). Then, 1.0M $BH_3$.THF (108 ml) was added slowly and the reaction mixture was slowly warmed up to −5° C. within 3–4 hours. The mixture was added to an ice cold 25% $NH_4OAc$ solution. The product was extracted into hot EtOAc, dried over $Na_2So_4$, concentrated to dryness and co-evaporated twice with toluene. It was dissolved in hot toluene and filtered through silica (~400 ml) with toluene and EtOAc:toluene 10:90 and 15:85. The product was finally recrystallized as a hydrate from toluene containing 4 mL $H_2O$. $[\alpha]_D$: +29.5° (c=1.82, $CHCl_3$).

Step 4: 3-(2-Acetylphenyl)-1(R)-(3-(2-(7-chloro-2-quinolinyl)ethenyl)phenyl)propanol At 0° C., a 1.5M MeMgBr solution in toluene:THF 1:1 (130 mL, 195 mmol) was added dropwise to a solution of the hydroxyester of Step 3 (11.04 g, 24.1 mmol) (dried in EtOAc and stripped with toluene to remove the $H_2O$) and MeOH (2.0 mL, 49.4 mmol) in 240 mL of anhydrous THF. The reaction mixture was stirred at r.t. for 2.5 h and was then poured into ice cold 25% $NH_4OAc$. The product was extracted into EtOAc, dried over $Na_2SO_4$ and purified by flash chromatography on silica with EtOAc:toluene 10:90 and 15:85. $[\alpha]_D$: +23.8° (c=1.04, $CHCl_3$).

Step 5: 1-(2-(3(R)-(3-(2-(7-Chloro-2-quinolinyl)ethenyl)phenyl)-3-(methylsulfonyloxy)propyl)phenyl)ethanone At −40° C., methanesulfonyl chloride (1.25 mL, 16.2 mmol) and $Et_3N$ (2.8 mL, 20 mmol) were added successively to a solution of the hydroxyketone of Step 4 (6.157 g, 13.44 mmol) in 135 mL of $CH_2Cl_2$ and the mixture was stirred at −40° C. for 30 min., then at 0° C.

for an hour. A saturated solution of NaHCO₃ was added and the title mesylate was extracted into CH₂CL₂, dried over Na₂SO₄, concentrated and the remaining traces of water were co-evaporated twice with toluene. This mesylate was used as such in Step 7.

Step 6: 3-Mercapto-2-(S)-methylpropanoic acid

A suspension of K₂CO₃ (7.5 g, 55 mmol) in 50 mL of MeOH was degassed by bubbling N₂ through it for 15 min. It was then cooled to −5° C., and NaBH₄ (38 mg, 1 mmol) was added. After 5 min, 3-(acetylthio)-2-(S)-methylpropanoic acid (4 g, 25 mmol) as added. The cold bath was removed. When the reaction reached r.t., glacial HOAc (7.5 mL, 125 mmol) was added slowly, and the reaction mixture was poured into a mixture of aq 10% HCl (25 mL) and brine (25 mL). Extraction with 2×50 mL CH₂Cl₂ followed by washing of the organic phase with HCl 10% (10 mL), brine (10 mL), drying over Na₂SO₄ and evaporation yielded a yellow residue. Kugelrohr distillation at 100° C./15 mm Hg yielded the title compound as a colorless oil.

¹H NMR (CDCl₃): δ1.30 (3H, d), 1.58 (1H, t), 2.8 (3H, m), 10.3 (1H, very br s). $[\alpha]_D -26.8°$ (c=2.0, MeOH). (Chem. Pharm. Bull 1982, 30, 3139 reported $[\alpha]_D -27.6°$ (c=2.0, MeOH).

Step 7: 3-((1(S)-(3-(2-(7-Chloro-2-quinolinyl)ethenyl)phenyl)-3-(2-acetylphenyl)propyl)thio-2(S)-methylpropanoic acid To a solution of the thiol of Step 6 (2.01 g, 16.7 mmol) in 15 mL of anhydrous DMSO:THF 2:1, 60% NaH in oil (1.62 g, 40.5 mmol) was added at 0° C. and the mixture was allowed to warm to r.t. for 15 min. To the suspension so obtained, 10 mL of anhydrous THF was added, followed by a solution of the mesylate of Step 5 (13.44 mmol) in 25 mL of anhydrous DMSO. After 2 h of stirring, the reaction mixture was poured into ice cold 25% NH4OAc. The product was extracted with EtOAc:THF 1:1 and the extracts were washed with brine and dried over Na₂SO₄. Flash chromatography of the residue on silica with EtOAc:toluene:HOAc 7.5:92.5:1 and 10:90:1 afforded the title compound as an oil.

¹H NMR (CD₃COCD₃): δ1.12 (3H, d), 2.20 (2H, q), 2.43 (1H, dd), 2.53 (3H, s), 2.54–2.85 (3H, m), 2.94 (1H, m), 4.02 (1H, t), 7.26–7.35 (2H, m), 7.47–7.56 (5H, m) 7.64 (1H, br d), 7.63–8.04 (6H, m), 8.35 (1H, d).

Step 8:

To the acid from Step 7 (4.77 g, 8.77 mmol) in EtOH 1N NaOH (8.8 mL) was added. The solvents were evaporated and the product was dissolved in H₂O and freeze-dried to yield the title compound.

Anal. Calc'd for C₃₂H₂₉ClNO₃SNa.0.6 H₂O: C, 66.62; H, 5.28; N, 2.43 Found C, 66.60; H, 5.09; N, 2.41.

EXAMPLES 2–16

Using the above methodology and that described in Schemes 1 through 4, the compounds of Examples 2–6 were prepared. In a similar way, the compounds of Examples 7–16 can also be prepared.

EXAMPLE 17

(R)-1-(((3-(2-acetylphenyl)-1-(3-(2-(7-chloro-2-quinolinyl)ethenyl)phenyl)propyl)thio)methyl)-cyclopropaneacetic acid, sodium salt Step 1: 1-(3-(2-(7-chloro-2-quinolinyl)ethenyl)phenyl)-2-propen-1-ol To a degassed suspension of 3-(2-(7-chloro-2-quinolinyl)ethenyl)benzaldehyde (U.S. Pat. No. 4,851,409, Example 24, Step 1) (100 g, 0.34 mol) in toluene (700 mL) at 0° C. was slowly added 1.0M vinylmagnesium bromide in toluene/THF (370 mL, 0.37 mol). After stirring for 1 hour at 0° C., the reaction was quenched by the slow addition of saturated NH₄Cl solution (150 mL), followed by H₂O (500 mL) and HOAc (50 mL). The product was extracted with EtOAc and the two-phase system was filtered through celite to remove an insoluble precipitate. The aqueous phase was then re-extracted with EtOAc (100 mL) and the combined organic layer was washed with H₂O, followed by brine. The solution was dried (MgSO₄), and evaporated to give a dark yellow residue which was purified by flash chromatography (EtOAc:hexane 1:5, then 1:3). The product was filtered from the column fractions to give a beige solid (67.6 g, mp=110°–112° C.). The filtrate was concentrated and the resulting residue was recrystallized from EtOAc/hexane 1:4 to give a second crop of 15.1 g.

Step 2: Methyl 2-(3-(3-(2-(7-chloro-2-quinolinyl)ethenyl)phenyl)-3-oxopropyl)benzoate A degassed suspension of 1-(3-(2-(7-chloro-2-quinolinyl)ethenyl)phenyl)-2-propen-1-ol (Step 1, 50.30 g, 156 mmol), LiOAc.2 H₂O (41.2 g, 404 mmol), LiCl (6.84 g, 161 mmol), Pd(OAc)₂ (1.00 g, 4.45 mmol) and methyl 2-bromobenzoate (33.5 g, 156 mmol) in 300 mL of DMF was stirred at 95° C. for 4 h. The mixture was cooled to r.t (room temperature) and added to 1.8 L of water. The product was extracted with hot EtOAc, dried over Na₂SO₄ and concentrated. It was dissolved in toluene and filtered through silica with toluene. Recrystallization in 1.2 L of EtOAc:hexanes 1:1 afforded 65.57 g of the title compound. Recrystallization of the mother liquors in 400 mL EtOAc:hexanes 1:3 afforded a further 8.30 g (86% overall yield) of the title material.

Step 3: Methyl (S)2-(3-(3-(2-(7-chloro-2-quinolinyl)ethenyl)phenyl)-3-hydroxypropyl)benzoate To a solution of (−)-B-chlorodiisopinocampheylborane (72.2 g, 0.225 mol) in THF (300 mL) cooled at −25° C. was added dropwise a solution of the ketone of Step 2 (68.5 g, 0.15 mol) in THF (350 mL). The red orange solution was stirred overnight at 15° C. and then poured into ice-water while stirring. The precipitate formed was collected and washed two times with water and then EtOAc. The solid was partitioned between CH₂Cl₂ (2.5 L) and 6% diethanolamine in water (1.2 L). The organic phases were washed with brine and dried over Na₂SO₄. The solvent was evaporated and 700 mL of MeOH was added. The product was crystallized by adding 70 mL of water slowly with vigourous stirring. The solid was collected and washed with MeOH:H₂O, 10:1 to yield the title compound (44.7 g, 65%).

¹H NMR (CDCl₃) δ2.10 (2H, m), 3.12 (3H, m), 3.90 (3H, S), 4.75 (1H, t), 7.22 to 7.55 (8H, m), 7.67 (4H, m), 7.92 (1H, d), 8.10 (2H, m).

Step 4: (S)-N-methyl-N-methoxy 2(3-(3-(2-(7-chloro-2-quinolinyl)ethenyl)phenyl)-3-hydroxypropyl)benzamide To a suspension of the hydroxy ester of Step 3 (4.519 g, 9.5 mmol) and N,O-dimethylhydroxylamine hydrochloride (2.777 g, 28.5 mmol) in 95 mL of anhydrous THF at 0° C. was added dropwise 3M EtMgBr in Et₂O (22 mL 66 mmol) over ≈40 min. The mixture was then stirred at 0° C. for 30 min. and poured into ice-cold saturated NH₄Cl. The product was extracted in EtOAc, dried over Na₂SO₄, and concentrated to yield the title compound.

Step 5: (S)-1-(2-(1-(3-(2-(7-chloro-2-quinolinyl)ethenyl)phenyl)-1-hydroxypropyl)phenyl)ethanone To a solution of the hydroxyamide of Step 4 (3.70 g, 7.60 mmol) in 80 mL of THF at 0° C. was added slowly 1.5M MeMgBr in THF:toluene 1:3 (25 mL, 37 mmol). The mixture was stirred at 0° C. for 30 min and at r.t. for 4 hr. It was added to cold saturated NH$_4$Cl and the product was extracted into EtOAc, dried over Na$_2$SO$_4$, and concentrated. Purification by flash chromatography on silica with EtOAc:toluene 15:85 and 20:80° afforded the title product. [α]$_D$= −24.0° (c=1, CHCl$_3$).

Step 6: (S)-1-(2-(1-(3-(2-(7-chloro-2-quinolinyl)ethenyl)phenyl)-1-(methanesulfonyloxy)propyl)phenyl)ethanone This mesylate was prepared from the alcohol of Step 5 using the procedure of Example 1, Step 5.

$^1$H-NHR (CDCl$_3$): δ8.12 (1H, d), 8.08 (1H, d) 7.75–7.25 (13H, m) 5.65 (1H, d), 3.10–2.90 (2H, m) 2.77 (3H, s), 2.59 (3H, s), 2.60 (3H, s) 2.45–2.15 (2H, m).

Step 7: 1,1-cyclopropanedimethanol

A solution of lithium aluminum hydride (50 g, 1.32 mol) in 1.6L of THF was cooled to −18° C. under N$_2$. A solution of diethyl 1,1-cyclopropanedicarboxylate (175 g, 0.94 mol) in 1.2L of THF was then added dropwise over 50 min, at such a rate that the internal temperature of the reaction remained below 10° C. The cooling bath was then removed, and after 15 min, the temperature had reached 15° C. The reaction was then quenched by careful addition of 50 mL H$_2$O, followed by 50 mL of 15% NaOH, and then 150 mL of H$_2$O. After the mixture turned white, it was filtered through celite, and the bed was washed with 4L of THF. Evaporation gave an oil which was distilled to give 81 g (0.79 mol, 84%) of the title compound as a colorless oil, b.p. 131°–138° C./15 mm Hg. $^1$H NMR (CDCl$_3$) δ0.48 (4H, s), 3.30 (2H, s), 3.58 (4H, s).

Step 8: 1-(hydroxymethyl)cyclopropanemethyl benzoate

To a solution of the diol of Step 7 (81 g, 0.79 mol) and pyridine (96 mL, 1.19 mol) in CH$_2$Cl$_2$ (1L) cooled at 0° C. was added slowly benzoyl chloride (121 mL, 1.03 mol). The reaction mixture was warmed to r.t. overnight and then poured in an aqueous solution of NH$_4$Cl. The products were extracted in CH$_2$Cl$_2$, washed with brine and dried over Na$_2$SO$_4$. The residual oil was purified by flash chromatography with 2:1 hexane:EtOAc and then 1:2 hexane:EtOAc to yield first, 116 g (47% yield) of the diester, then 89 g (54% yield) of the title alcohol.

$^1$H NMR (CDCl$_3$) δ0.65 (4H, m), 2.20 (1H, t), 3.53 (2H, d), 4.35 (2H, s), 7.45 (2H, m), 7.60 (1H, m), 8.07 (2H, m).

Step 9: 1-(benzoyloxymethyl)cyclopropaneacetonitrile

To a solution of the alcohol of Step 8 (80 g, 0.388 mol) and triethylamine (162 mL, 1.16 mol) in CH$_2$Cl$_2$ (1.5L) cooled at −40° C. was added methanesulfonyl chloride (75 mL, 0.504 mol). The reaction mixture was warmed to −10° C. for 20 min and then poured into an aqueous solution of NaHCO$_3$ and extracted with CH$_2$Cl$_2$. The organic phases were washed with brine and dried over Na$_2$SO$_4$. The residual oil was then dissolved in DMSO (1.5L) and sodium cyanide was added (86 g, 1.76 mol) portionwise. The reaction mixture was stirred at r.t. for 3 days then poured in an aqueous solution of NaHCO$_3$ and extracted with Et$_2$O. The organic phases were washed with brine and dried over Na$_2$SO$_4$. Evaporation of the solvent afforded the title product.

$^1$H NMR (CDCl$_3$) δ0.80 (4H, m), 2.62 (2H, s), 4.27 (2H, s), 7.48 (2H, m), 7.60 (1H, m), 8.08 (2H, m).

Step 10: Methyl 1-(hydroxymethyl)cyclopropaneacetate

The nitrile of Step 9 (0.388 mol) was dissolved in ethanol (400 mL), 8N KOH (800 mL) was added and the reaction mixture was heated to reflux overnight. Most of the ethanol was evaporated and ice was added to the mixture. Concentrated HCl was added (600 mL) dropwise at 0° C. (without warming over 10° C. inside the solution) until obtention of pH≃1. The acidic solution was then extracted with EtOAc two times and the organic phases were washed 2 times with brine and dried over Na$_2$SO$_4$. The solvent was evaporated and the solid was dissolved in THF (500 mL). A solution of diazomethane in Et$_2$O (about 1.7L, 0.85 mol) was added at 0° C. until the yellow color remained and no more acid could be seen by TLC. The solvent was evaporated and the residual oil was purified by flash chromatography using 1:1 to 2:1 EtOAc:hexane to yield 28.2 g, (50% yield) of the title compound.

$^1$H NMR (CDCl$_3$) δ0.55 (4H, m), 2.45 (2H, s), 2.55 (1H, t), 3.5 (2H, d), 3.70 (3H, s).

Step 11: Methyl 1-(acetylthiomethyl)cyclopropaneacetate

To a solution of the alcohol of Step 10 (28.2 g, 0.20 mol) and triethylamine (82 mL, 0.59 mol) in dichloromethane (1L) cooled to −40° C. was added methanesulfonyl chloride (43.5 mL, 0.3 mol). The reaction mixture was warmed to −10° C. for 20 min and then an aqueous solution of NaHCO$_3$ was added. The product was extracted with CH$_2$Cl$_2$, washed with brine and dried over Na$_2$SO$_4$. A portion of this mesylate (0.053 mol) was then dissolved in DMF (180 mL) and cooled to 0° C. Freshly prepared cesium thiol acetate (J. Org. Chem., 51, 3664, (1986)) (22 g, 0.11 mol) was added and the mixture was stirred overnight at r.t. The reaction mixture was poured into an aqueous solution of NaHCO$_3$ and extracted with Et$_2$O. The organic phases were washed with brine and dried over Na$_2$SO$_4$. The residual oil was then purified by flash chromatography with 10:1 hexane:EtOAc to yield 7.5 g, 70%, of the title compound.

$^1$H NMR (CDCl$_3$) δ0.60 (4H, m), 2.30 (2H, s), 2.35 (3H, s), 3.03 (2H, s), 3.70 (3H, s).

Step 12: Methyl (R)-1-(((3-(2-acetylphenyl)-1-(3-(2-(7-chloro-2-quinolinyl)ethenyl)phenyl) propyl)thio)methyl)cyclopropaneacetate To a degassed solution of methyl 1-(acetylthiomethyl)cyclopropane acetate (364 mg, 1.8 mmol) (from Step 11) in 4 mL of acetonitrile was added hydrazine (90 μL, 2.8 mmol) at 0° C. The solution was stirred at 0° C. for 30 min. and transferred via syringe to a degassed mixture of the mesylate (from Step 6) (608 mg, 1 mmol) and Cs$_2$CO$_3$ (1 g, 3 mmol) in 3 mL of CH$_3$CN at 0° C. The mixture was warmed up to r.t. while stirring, and stirred at r.t. for 40 min. For the workup the reaction mixture was poured into cold aqueous NH$_4$Cl and extracted with EtOAc. The EtOAc solution was separated, washed once with brine, and dried over Na$_2$SO$_4$. The crude product was purified by flash chromatography with 6:1 toluene:EtOAc to yield 490 mg (84%) of the title compound.

$^1$H-NHR (CDCl$_3$): δ8.05 (1H, d), 8.01 (1H, d), 7.70–7.10 (13H, m), 3.83 (1H, t), 3.56 (3H, s), 3.0–2.68 (2H, m), 2.48 (4H, s), 2.40 (2H, s), 2.38–2.28 (2H, AB-System) 2.18–2.04 (2H, m), 0.47–0.30 (4H, m).

Step 13: (R)-1-(((3-(2-acetylphenyl)-1-(3-(2-(7-chloro-2-quinolinyl)ethenyl)phenyl)propyl)thio)methyl)cyclopropaneacetic acid To a solution of the methyl ester (from Step 12) (490 mg, 0.84 mmol) in MeOH (12 mL) and THF (4 mL) was added NaOH (2M, 2 mL) at r.t. The reaction solution was stirred at r.t. for 6 hrs., neutralized with HOAc and partitioned between EtOAc and brine. The EtOAc was separated, washed once with brine, dried over $Na_2SO_4$, and evaporated. The crude product was purified by flash chromatography initially with 2.5:1 hexane:EtOAc, followed by 2.5:1:0.05 hexane:EtOAc:HOAc to afford 412 mg (86%) of the title acid.

$^1$H-NMR ($CDCl_3$): δ8.07 (1H, d), 8.01 (1H, d), 7.73–7.10 (13H, m), 3.90 (1H, t), 3.05–2.74 (2H, m), 2.67 (1H, d), 2.61 (1H, d), 2.51 (3H, s), 2.36–2.23 (2H, m), 2.11 (2H, q), 0.50–0.44 (4H, m).

The title compound was prepared from the acid of Step 13 as per Example 1, Step 8.

Anal. Calcd. for $C_{34}H_{31}ClNNaO_3S.2\ H_2O$: C, 65.01; H, 5.62; N, 2.23. Found: C, 65.03; H, 5.45; N, 2.19.

What is claimed is:

1. A compound of the formula:

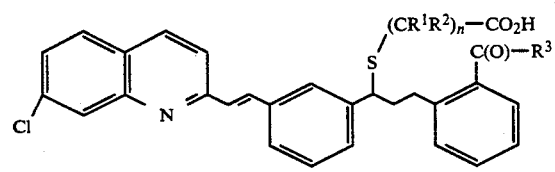

wherein:
each of $R^1$ and $R^2$ is independently H or lower alkyl with the proviso that at least one is lower alkyl, or $R^1$ and $R^2$ attached to the same carbon are a ring of 3 to 6 carbon atoms;
$R^3$ is $C_1$–$C_3$ alkyl: and
n is 1 to 4;

or a pharmaceutically acceptable salt thereof.

2. The compound sodium 3-((1(S)-(3-(2-(7-chloro-2-quinolinyl)ethenyl)phenyl)-3-(2-acetylphenyl)propyl)-thio)-2(S)-methylpropanoate.

3. A pharmaceutical composition comprising a therapeutically effective amount of a compound of claim 1 and a pharmaceutically acceptable carrier.

4. A method of preventing the synthesis, the action, or the release of SRS-A or leukotrienes in a mammal which comprises administering to said mammal an effective amount of a compound of claim 1.

5. The method of claim 4 wherein the mammal is man.

6. A method of treating asthma in a mammal comprising administering to a mammal in need of such treatment a therapeutically effective amount of a compound of claim 1.

7. The method of claim 6 wherein the mammal is man.

8. A method of treating inflammatory diseases of the eye in mammal which comprises administering to a mammal in need of such treatment a therapeutically effective amount of a compound of claim 1.

9. A compound of claim 1 of the formula:

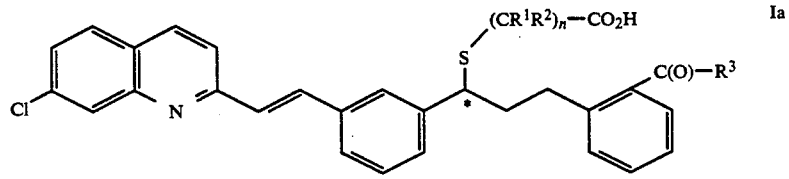

wherein the substituents are as follows:

| No. | $(CR^1R^2)n$ | Stereo * | $R^3$ |
|---|---|---|---|
| 1 | $CH_2(S)CH(CH_3)$ | (S) | $CH_3$ |
| 2 | $CH_2(S)CH(CH_3)$ | (S) | $CH_2CH_3$ |
| 4 | rac-$CH(CH_3)CH_2$ | (R) | $CH_3$ |
| 6 | $CH_2(S)CH(CH_2CH_3)$ | (S) | $CH_3$ |
| 7 | (S)$CH(CH_3)CH_2$ | (R) | $CH_3$ |
| 8 | (R)$CH(CH_3)CH_2$ | (R) | $CH_3$ |
| 9 | $CH_2C(CH_3)_2CH_2$ | (R) | $CH_3$ |
| 10 | (S)$CH(CH_3)CH_2CH_2$ | (R) | $CH_3$ |
| 12 | (S)$CH(CH_2CH_3)CH_2$ | (R) | $CH_3$ |
| 13 | (R)$CH(CH_2CH_3)CH_2$ | (R) | $CH_3$ |
| 15 | (S)$CH(CH_3)$(S)$CH(CH_3)$ | (R) | $CH_3$ |
| 17 | $CH_2C(CH_2CH_2)CH_2$ | (R) | $CH_3$ |

* * * * *